(12) United States Patent
Konoshima et al.

(10) Patent No.: US 11,443,012 B2
(45) Date of Patent: Sep. 13, 2022

(54) OPTIMIZATION APPARATUS, METHOD IMPLEMENTED BY OPTIMIZATION APPARATUS, AND NON-TRANSITORY COMPUTER-READABLE STORAGE MEDIUM FOR STORING PROGRAM

(71) Applicant: FUJITSU LIMITED, Kawasaki (JP)

(72) Inventors: Makiko Konoshima, Kawasaki (JP); Jun Ohkubo, Saitama (JP)

(73) Assignee: FUJITSU LIMITED, Kawasaki (JP)

( * ) Notice: Subject to any disclaimer, the term of this patent is extended or adjusted under 35 U.S.C. 154(b) by 173 days.

(21) Appl. No.: 16/569,077

(22) Filed: Sep. 12, 2019

(65) Prior Publication Data

US 2020/0133988 A1 Apr. 30, 2020

(30) Foreign Application Priority Data

Oct. 24, 2018 (JP) .............................. JP2018-199994

(51) Int. Cl.
*G06F 17/14* (2006.01)
*G06F 17/16* (2006.01)
(Continued)

(52) U.S. Cl.
CPC .............. *G06F 17/14* (2013.01); *G06F 17/11* (2013.01); *G06F 17/16* (2013.01); *G06N 10/00* (2019.01)

(58) Field of Classification Search
CPC ......... G06F 17/11; G06F 17/14; G06N 5/003; G06N 10/00
See application file for complete search history.

(56) References Cited

U.S. PATENT DOCUMENTS 6,560,311 B1 5/2003 Shepard et al.
2017/0242824 A1* 8/2017 Karimi .................. G06N 5/003

FOREIGN PATENT DOCUMENTS

JP 10-149445 6/1998
JP 2002-522128 7/2002
(Continued)

OTHER PUBLICATIONS

V.S. Denchev et al., "Robust classification with adiabatic quantum optimization", in Proc. ICML'12, 8 pages, 2012.
(Continued)

*Primary Examiner* — Matthew D Sandifer
*Assistant Examiner* — Huy Duong
(74) *Attorney, Agent, or Firm* — Staas & Halsey LLP

(57) ABSTRACT

An optimization apparatus includes: a memory; and a processor coupled to the memory, the processor being configured to (a): execute transformation processing that includes transforming an input first cost function to a second cost function by using at least any one of "Legendre transformation," "Lagrange function," and "Wolfe's duality theorem," (b): execute binary expansion processing that includes acquiring values in an Ising format by carrying out binary expansion for values relating to coefficients of the second cost function, (c): execute Ising machine processing that includes seeking values that represent a ground state regarding the values in the Ising format relating to the coefficients of the second cost function, and (d): execute reverse binary expansion processing that includes acquiring values that minimize the first cost function by carrying out reverse binary expansion for the sought values that represent the ground state.

3 Claims, 15 Drawing Sheets

(51) Int. Cl.
*G06F 17/11* (2006.01)
*G06N 10/00* (2022.01)

(56) References Cited

FOREIGN PATENT DOCUMENTS

| WO | 00/07668 | 2/2000 |
| WO | 2017/145086 A1 | 8/2017 |

OTHER PUBLICATIONS

Nazareth et al., "First application of quantum annealing to IMRT beamlet intensity optimization", Physics in Medicine and Biology, Institute of Physics and Engineering in Medicine, Bristol GB, vol. 60, No. 10, May 1, 2015, pp. 4137-4148**.
Denchev et al., "Robust Classification with Adiabatic Quantum Optimization", CORR (ARXIV), vol. 1285.1148, No. v2, May 30, 2012, pp. 1-17**.
Extended European Search Report dated Mar. 20, 2020 from European Application No. 19196985.6, 9 pages.
European Office Action dated Jan. 21, 2021 from European Application No. 19196985.6, 6 pages.

* cited by examiner

| | DISEASE P(5) | |
|---|---|---|
| | NORMAL P(1) | DISEASE P(3) |
| DISEASE P(2) | DISEASE P(4) | |

$S^M$

| 0.074 | 0.122 | 0.139 | 0.056 | 0.076 | 0.171 | 0.178 | 0.124 | 0.022 | 0.127 | 0.131 | 0.005 | 0.003 | 0.096 | 0.105 | 0.104 | 0.133 | 0.121 | 0.158 | 0.003 |
| 0.186 | 0.002 | 0.095 | 0.068 | 0.082 | 0.097 | 0.041 | 0.014 | 0.077 | 0.155 | 0.168 | 0.114 | 0.106 | 0.036 | 0.008 | 0.104 | 0.138 | 0.113 | 0.103 | 0.068 |
| 0.174 | 0.092 | 0.089 | 0.131 | 0.139 | 0.036 | 0.11 | 0.086 | 0.02 | 0.187 | 0.075 | 0.091 | 0.189 | 0.189 | 0.189 | 0.043 | 0.073 | 0.139 | 0.098 | 0.068 |
| 0.118 | 0.04 | 0.079 | 0.086 | 0.011 | 0.124 | 0.053 | 0.033 | 0.019 | 0.124 | 0.058 | 0.178 | 0.131 | 0.09 | 0.132 | 0.028 | 0.014 | 0.103 | 0.18 | 0.129 |
| 0.178 | 0.051 | 0.077 | 0.092 | 0.103 | 0.132 | 0.138 | 0.063 | 0.093 | 0.042 | 0.137 | 0.12 | 0.031 | 0.093 | 0.09 | 0.14 | 0.172 | 0.098 | 0.026 | 0.164 |

| P | Ci | MWabs | MWsquare |
|---|---|---|---|
| 0.574 | 0.584 | 0.583 | 0.631 |
| 1.117 | 1.127 | 0.789 | 0.884 |
| 0.814 | 0.824 | 0.768 | 0.873 |
| 0.945 | 0.955 | 0.665 | 0.791 |
| 0.964 | 0.974 | 0.881 | 0.896 |

FIG. 15
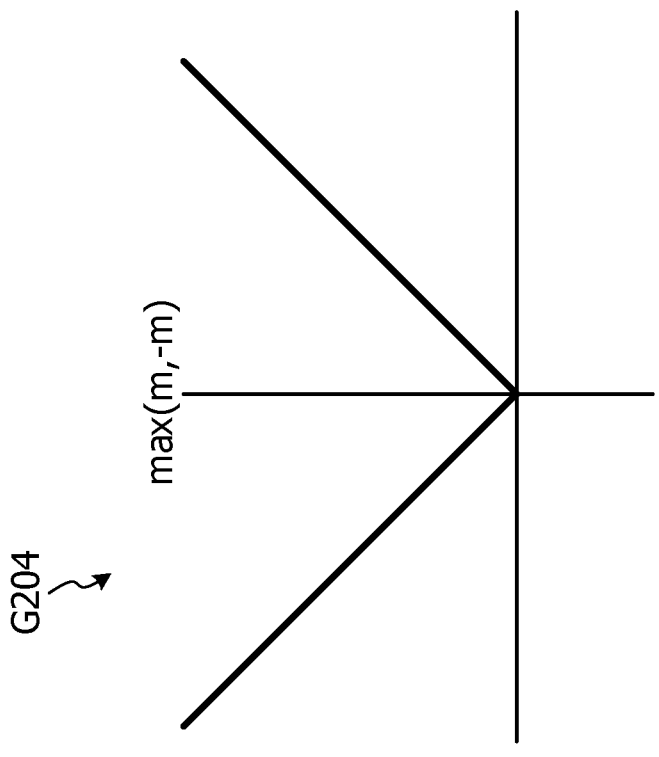
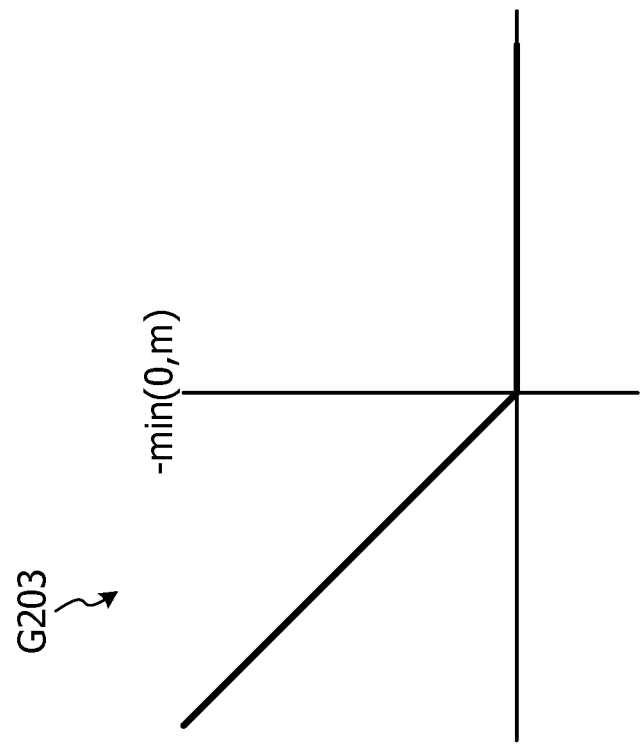

OPTIMIZATION APPARATUS, METHOD IMPLEMENTED BY OPTIMIZATION APPARATUS, AND NON-TRANSITORY COMPUTER-READABLE STORAGE MEDIUM FOR STORING PROGRAM

CROSS-REFERENCE TO RELATED APPLICATION

This application is based upon and claims the benefit of priority of the prior Japanese Patent Application No. 2018-199994, filed on Oct. 24, 2018, the entire contents of which are incorporated herein by reference.

FIELD

The embodiments discussed herein are related to an optimization apparatus, a method implemented by an optimization apparatus, and a non-transitory computer-readable storage medium storing a program.

BACKGROUND

As a method for solving a multivariable optimization problem, at which the von Neumann computer is not good, the Ising machine (referred to as Boltzmann machine in some cases) using the Ising energy function (referred to also as cost function or objective function) exists. In the Ising machine, a problem of a calculation target is replaced by an Ising model that is a model representing the behavior of spins of a magnetic body and calculation is carried out. For example, the Ising machine finds, as a solution, the combination of the states of the respective bits with which the minimum value of the above-described energy function is obtained (ground state) by simulated annealing (referred to also as SA).

Regarding the replacement of the problem of the calculation target into the Ising model, a related art is known in which the problem is replaced by the Ising model through an approximation by the q-loss function because transformation to the Ising model is difficult if a term of a discontinuous function exists in a cost function deemed as the problem.

Examples of the related art include Japanese Laid-open Patent Publication, No. 10-149445, Japanese National Publication of International Patent Application No. 2002-522128, and V. S. Denchev, N. Ding, S. V. N. Vishwanathan, and H. Neven, "Robust classification with adiabatic quantum optimization," in Proc. ICML'12, pp. 1003-1010 (2012).

SUMMARY

According to an aspect of the embodiment, an optimization apparatus includes: a memory; and a processor coupled to the memory, the processor being configured to (a): execute transformation processing that includes transforming an input first cost function to a second cost function by using at least any one of "Legendre transformation," "Lagrange function," and "Wolfe's duality theorem," (b): execute binary expansion processing that includes acquiring values in an Ising format by carrying out binary expansion for values relating to coefficients of the second cost function, (c): execute Ising machine processing that includes seeking values that represent a ground state regarding the values in the Ising format relating to the coefficients of the second cost function, and (d): execute reverse binary expansion processing that includes acquiring values that minimize the first cost function by carrying out reverse binary expansion for the sought values that represent the ground state.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 7 is an explanatory diagram explaining one example of an experimental result;

FIG. 15 is an explanatory diagram exemplifying discontinuous functions.

DESCRIPTION OF EMBODIMENTS

However, in the above-described related art, the discontinuous function is replaced by another function obtained through the approximation by the q-loss function. Therefore, there is a problem that a difference arises between the solution found by the Ising machine and the value desired to be found originally and a solution with high accuracy is not obtained in some cases.

Figure 10:
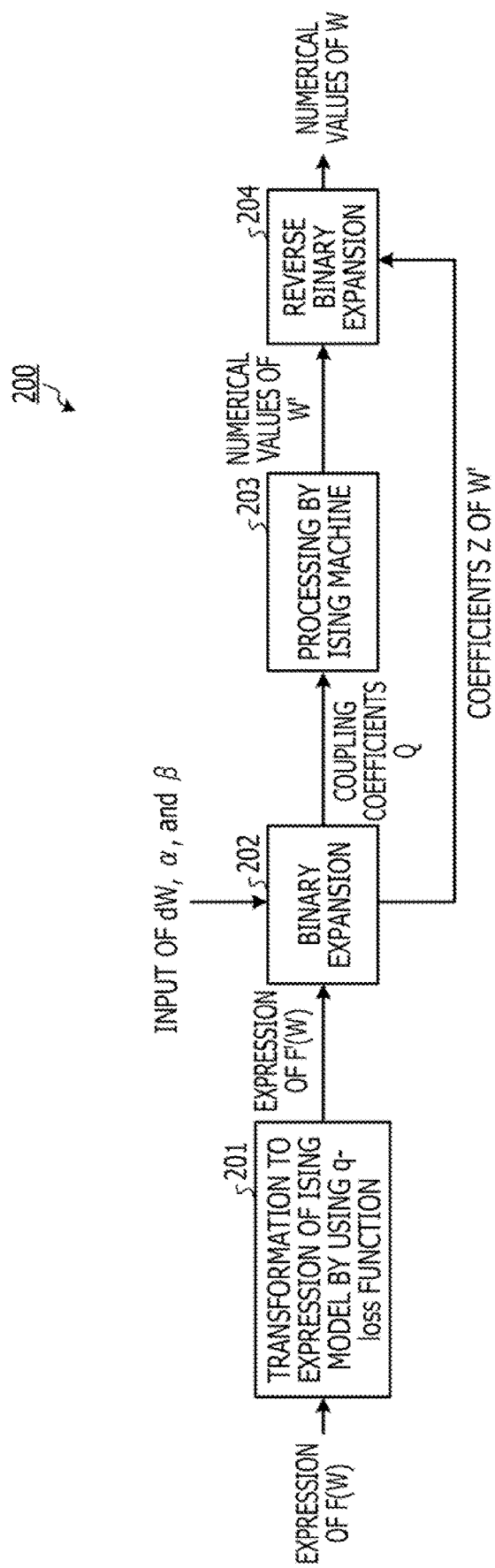
FIG. 10 is a block diagram illustrating a functional configuration example of existing optimization apparatus.

FIG. 10 is a block diagram illustrating a functional configuration example of existing optimization apparatus. As illustrated in FIG. 10, in an optimization apparatus 200, input of a cost function F(W) relating to an optimization problem is accepted and transformation to an expression of an Ising model (F'(W)) is carried out by using a q-loss function (201). As the cost function F(W) relating to the optimization problem, a cost function relating to formulation of a radiation irradiation plan in the medical field exists as one example.

Figure 11:
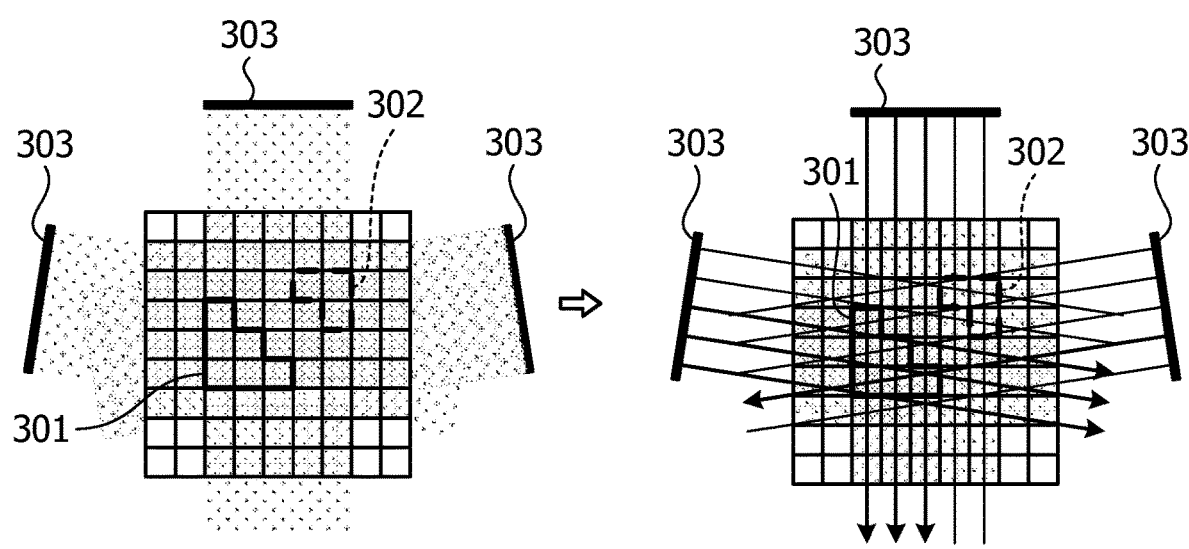
FIG. 11 is an explanatory diagram explaining a formulation example of a radiation irradiation plan.

FIG. 11 is an explanatory diagram explaining a formulation example of a radiation irradiation plan. As illustrated in FIG. 11, in intensity modulated radiation therapy (IMRT), the shape of a multileaf collimator 303 is changed and each of regions such as a tumor 301 and normal tissue 302 is irradiated with radiation whose intensity is changed with a fine solution in conformity to the shape of a part that is not blocked by the multileaf collimator 303. The radiation irradiation plan in this case may be regarded as an optimization problem of carrying out irradiation of the tumor 301 while reducing irradiation of the normal tissue 302.

A cost function (F(W)) relating to this radiation irradiation plan is as follows. Here, the irradiation target (tumor 301 or normal tissue 302) in FIG. 11 is explained as a two-dimensional irradiation target and is expanded into a one-dimensional irradiation target in the following. Thus, suppose that the following description is similar even when the irradiation target is a three- or more-dimensional irradiation target.

First, the irradiation target is discretized (segmentation by squares in the illustrated example) and is turned to pixels lined up on one row. Here, the number of pixels is defined as I. Furthermore, suppose that N beams of the radiation exist, and the intensity thereof is represented by a vector W=(w1, w2, . . . , wN).

When the irradiation amount of the radiation at the i-th pixel is defined as $d_i(W, M_i)$, $d_i(W, M_i)$ is represented by the following expression (1).

$$d_i(W,M_i) = \Sigma_{n=1}^N w_n M_{in} \quad (1)$$

In expression (1), Min is the influence given to the i-th pixel by the n-th beam and may be calculated in advance. Furthermore, $M_i=(M_{i1}, M_{i2}, \ldots, M_{iN})$ is defined.

If a target irradiation amount ($p_i$) is given for each pixel, the cost function F(W) relating thereto is represented by the following expression (2), with the target irradiation amount defined as $M=(M_1, M_2, \ldots, M_i)$. The purpose of squaring in expression (2) is to transform the function to an Ising model and ignore the sign of the difference in finding the minimum W when $p_i$ and $d_i(W, M_i)$ become the closest values.

$$F(W) = \Sigma_i(p_i - di(W,M_i))^2 \quad (2)$$

However, there is a limit to the irradiation amount depending on the organ. When the limit is put as Ci, the cost function F(W) is represented by the following expression (3).

$$F(W) = \Sigma_i(p_i - d_i(W,M_i))^2 + \Sigma_i \beta_i \max(0, d_i(W) - C_i) \quad (3)$$

The vector W of the intensity of the beams that minimizes the cost function F(W) represented in the expression (3) is the solution found as the optimization problem. Here, $p_i$, $M_i$, $\beta_i$, and $C_i$ are constants set by a user. Furthermore, the first term in the cost function F(W) represented in expression (3) is a term (C(W)) that is a continuous function. The second term is a constraint term (F1(W)) and βi represents the intensity of the constraint term about each pixel. When di(W) becomes larger beyond Ci, F(W) also becomes larger. Furthermore, the second term is a discontinuous step function and therefore it is difficult to express F(W) in the Ising form without change.

Thus, in the processing (201) of transforming the cost function F(W) to the expression of the Ising model (F'(W)), F1(W) included in F(W) is squared to be replaced by a q-loss function and F'(W) expressed in the two-body Ising format is output.

Figure 12:
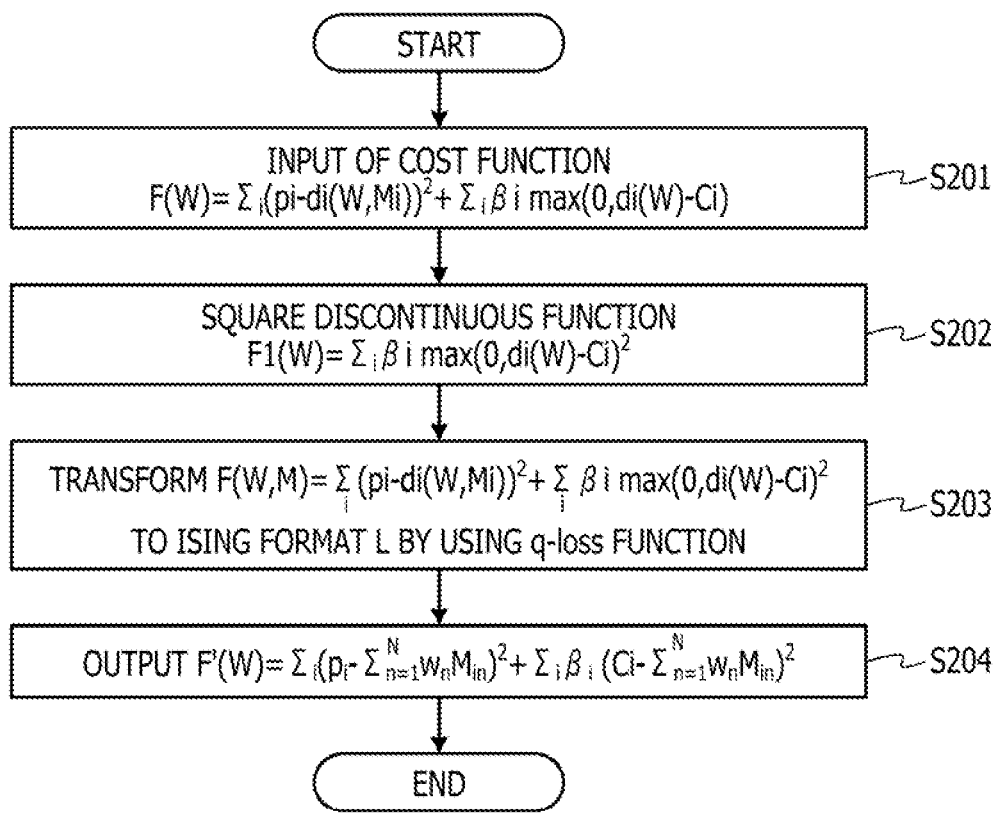
FIG. 12 is a flowchart illustrating an existing example of transformation to an expression of an Ising model.

FIG. 12 is a flowchart illustrating an existing example of transformation to the expression of an Ising model. As illustrated in FIG. 12, when the processing is started, the optimization apparatus 200 accepts input of the cost function F(W) represented in expression (3) (S201).

In the cost function F(W), F1(W) that is a discontinuous function is included. Furthermore, the number of pixels (I), the number of beams (N), the target irradiation amount ($p_i$), the degree of influence given by the beam ($M_i$), the strength of the constraint ($\beta_i$), and the limit amount of irradiation ($C_i$) are included in the cost function F(W) as constants. These constants are specified by a user.

Subsequently, for processing with the q-loss function, the optimization apparatus 200 squares the discontinuous function (F1(W)) included in the cost function F(W) (S202).

Next, the optimization apparatus 200 transforms the cost function F(W) in which the discontinuous function (F1(W)) is squared to the Ising format by using the q-loss function (S203). Subsequently, the optimization apparatus 200 outputs the transformed F'(W) (S204).

The q-loss function may be first written as represented in the following expression (4) with use of a parameter ($q \in [-\infty, 0]$).

$$L_q(m) = \min[(1-q)^2, (\max[0, 1-m])^2] \quad (4)$$

Here, when a variable ($t \in R$) is added and the q-loss function is rewritten into the Ising format, the q-loss function is represented by the following expression (5).

$$L_q(m) = \min_t \left\{ (m-t)^2 + (1-q)^{2\frac{(1-\text{sign}(t-1))}{2}} \right\} \quad (5)$$

Here, assuming $q \ll 0$, expression (4) becomes $L_q(m) = (\max[0, 1-m])^2$. Therefore, F1 included in F is represented by the following expression (6) by using $L_q$.

$$F(w) = \sum_i (p_i - d_i(w))^2 + \sum_i \beta_i (\max[0, d_i(w) - C_i])^2 \quad (6)$$

$$= \sum_i \left( p_i - \sum_{n=1}^N w_n M_{in} \right)^2 +$$

$$\sum_i \beta_i \left( \max\left[ 0, 1 - \left(1 + C_i - \sum_{n=1}^N w_i M_{in}\right) \right] \right)^2$$

$$\cong \sum_i \left( p_i - \sum_{n=1}^N w_n M_{in} \right)^2 + \sum_i \beta_i L_q \left( 1 + C_i - \sum_{n=1}^N w_n M_{in} \right)$$

Furthermore, in the Ising format, when $q \ll 0$ and a condition of $t_i \geq 1$ that is the minimal condition are added, the following expression (7) is obtained.

$$F(w, t) = \sum_i \left( p_i - \sum_{n=1}^N w_n M_{in} \right)^2 + \quad (7)$$

$$\sum_i \beta_i \left\{ \left( \left(1 + C_i - \sum_{n=1}^N w_n M_{in}\right) - t_i \right)^2 + (1-q)^{2\frac{1-\text{sign}(t_i-1)}{2}} \right\}$$

In the expression (7), t is set to a constant 1 (canceled out with the constant term 1) and F'(W) of the following expression (8) is obtained. In the F'(W), the constraint term is represented in the square form. The optimization apparatus 200 outputs the obtained F'(W).

$$F'(w) = \Sigma_i (p_i - \Sigma_{n=1}^N w_n M_{in})^2 + \Sigma_i \beta_i (C_i - \Sigma_{n=1}^N w_n M_{in})^2 \quad (8)$$

Referring back to FIG. 10, because the transformed F'(W) remains continuous values, the optimization apparatus 200 subjects W to binary expansion into 0 and 1 for processing by the Ising machine (202). For example, the optimization apparatus 200 accepts input of the precision of the binary expansion (dw) and the range of values ($\alpha, \beta$) and carries out the binary expansion of W. Subsequently, the optimization apparatus 200 outputs coupling coefficients (Q) relating to W' resulting from the binary expansion and coefficients (Z) for returning W' to the original real numbers.

Figure 13:
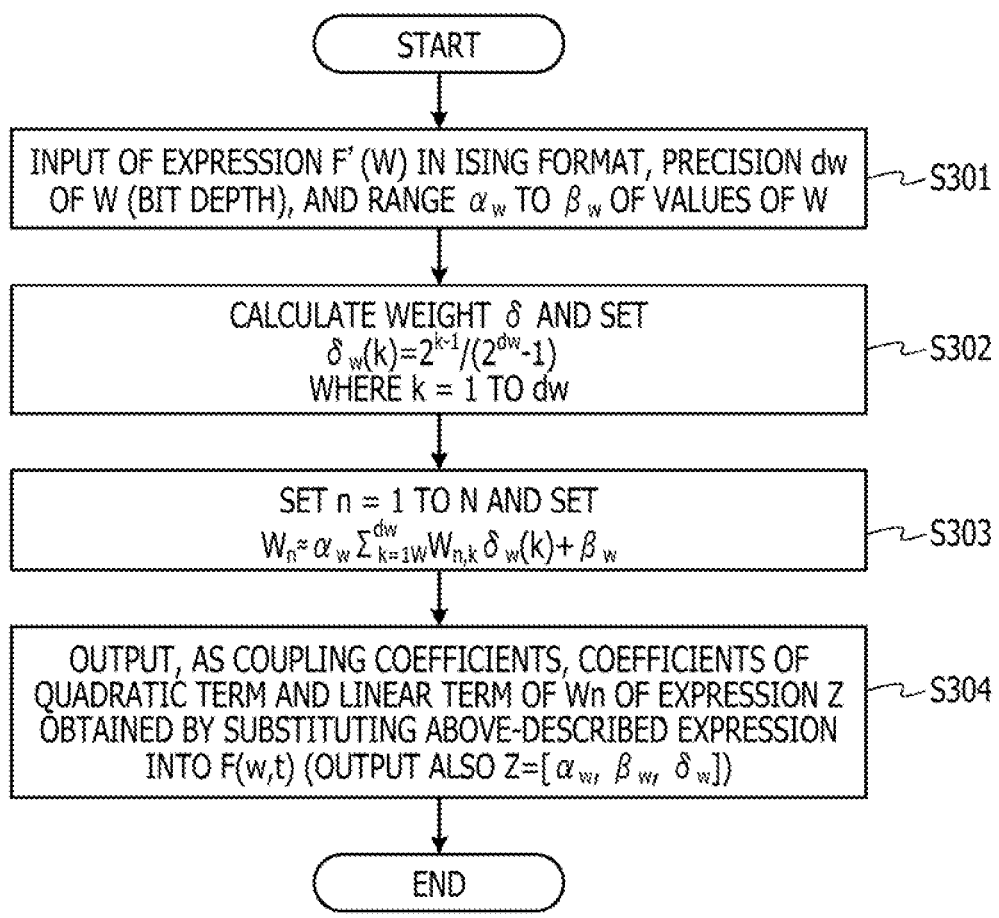
FIG. 13 is a flowchart illustrating one example of binary expansion processing.

FIG. 13 is a flowchart illustrating one example of binary expansion processing. As illustrated in FIG. 13, when the processing is started, the optimization apparatus 200 accepts input of the transformed expression in the Ising format (F'(W)), the precision dw of W (bit depth), and the range $\alpha_w$ to $\beta_w$ of the values of W (S301). Here, dw and $\alpha_w$ to $\beta_w$ are numerical values given by the user.

Subsequently, the optimization apparatus 200 calculates the weight ($\delta$) of each bit obtained as the result of the binary expansion and sets $\delta_w(k)=2^{k-1}/(2^{k-1}-1)$ (S302). In this expression, k=1 to dw is satisfied.

For example, when binary expansion is carried out with bit precision (dd) for what is obtained by turning the numerical values W to binary numbers, a string wd in which the MSB is set on the left side and numerical values are turned to binary numbers for the dd bits is defined as wnd=[wd1, wd2, . . . , wddd]. The weight $\delta_w$ corresponding thereto is represented by the following expression (9) through multiplication of the expanded bits and the weights.

$$\delta_w = [2^{dd-1}, 2^{dd-2}, \ldots, 2^1, 2^0]/(2^{dd}-1) \tag{9}$$

Subsequently, when the optimization apparatus 200 sets the section of Wn to $\alpha w$ to $\beta w$ and simultaneously limits the range in the binary expansion, Wn is represented by the following expression (10).

$$W_n \approx (\alpha w - \beta w)(\delta_w[1]*wd[1] + \delta_w[2]*wd[2] + \ldots + \delta_w[dd]*wd[dd]) + \beta w \tag{10}$$

For example, the optimization apparatus 200 sets n=1 to N and sets $W_n = \alpha_w \Sigma_{k=1}^{dw} W_{n,k} \delta_w(k) + \beta_w$ (S303). $W_{n,k}$ is what is obtained by turning Wn to binary values and is numerical values of 0 or 1 and corresponding to the Ising spins.

Subsequently, the optimization apparatus 200 outputs, as the coupling coefficients, the coefficients of the quadratic term and the linear term of Wn of the expression (Z) obtained by substituting the above-described expression into F(w, t) (S304). At this time, the optimization apparatus 200 also outputs Z=[$\alpha w, \beta w, \delta w$].

For example, all terms of F' are subjected to summation regarding i and therefore are added to each other finally. First, a consideration will be made about the terms inside the total sum. Here, when $A = \Sigma_{k=1}^N W_n M_n$ is defined, the inside of F' is represented by the following expression (11).

$$(p-A)^2 + \beta(C-A)^2 = (1+\beta)A^2 - 2(P+\beta C)A + p^2 + \beta C^2 \tag{11}$$

Here, Sr=[$W_1, W_2, \ldots, W_N$] and M=[$M_1, M_2, \ldots, M_N$] are defined.

In expression (11), $(1+\beta)A^2$ is the quadratic term and corresponds to the following coupling coefficient (Jr). Furthermore, $-2(P+\beta C)A$ is the linear term and corresponds to the following coupling coefficient hr. Moreover, $p^2 + \beta C^2$ is a constant term and has no relation to W and therefore will be ignored in the following.

The expression of the Ising model before the binary expansion (S is the Ising spin and is a real number) and the coupling coefficients Jr and hr are represented by the following expression (12).

$$\Sigma_{KL=1}^N Jr_{KL} Sr_K Sr_L + \Sigma_{K=1}^N hr_K Sr_K \tag{12}$$

Thus, the coupling coefficients Jr and hr are represented by the following expressions (13) and (14).

$$hr = [-2(P+\beta C)M_1 - 2(P+\beta C)M_2 \ldots -2(P+\beta C)M_N] \tag{13}$$

$$Jr = \begin{bmatrix} (1+\beta)M_1^2 & (1+\beta)M_1 M_2 \\ (1+\beta)M_1 M_2 & (1+\beta)M_2^2 \end{bmatrix} \tag{14}$$

Sr is a real number and therefore binary expansion is carried out. What results from the binary expansion is what is obtained by lining up elements resulting from binary expansion of each element of Sr in the row direction. Here, what results from the binary expansion of Sr is defined as S=[$W_{1,1}, W_{1,2}, \ldots, W_{N,d}$]. When each element of Jr is multiplied by the weight $\delta_w$ and the matrix of Jr is expanded by a factor of N in the row direction and the column direction, what results from the binary expansion of Jr is represented by the following expression (15).

$$J' = \begin{bmatrix} (1+\beta)M_1^2 \delta_1 & \ldots & (1+\beta)M_1^2 \delta_d & \ldots \\ \vdots & \ldots & \vdots & \ldots \\ (1+\beta)M_1^2 \delta_d & \ldots & (1+\beta)M_1^2 \delta_d & \\ (1+\beta)M_1 M_2 \delta_1 & & \ldots & \\ \vdots & & \vdots & \end{bmatrix} \tag{15}$$

Similarly, also regarding hr, each element of hr is multiplied by the weight $\delta_w$ and the vector is expanded by a factor of N in the row direction. When the resulting vector is defined as h', h' is represented by the following expression (16).

$$h' = [-2(P+\beta C)M_1 \delta_1, \ldots, -2(P+\beta C)M_1 \delta_d, \ldots, -2(P+\beta C)M_N \delta_d] \tag{16}$$

Regarding the pixel (i), W as the basis of S is invariable. Regarding J' and h', what are finally obtained are what result from addition of i elements to each other with respect to each element and are represented by the following expressions (17) and (18). The number of bits of S is N*d in total.

$$J = \begin{bmatrix} (1+\beta)\left(\sum_{i=1}^{I} M_{i1}^2\right)\delta_{d1} & \ldots & (1+\beta)\left(\sum_{i=1}^{I} M_{i1}^2\right)\delta_{dd} & \ldots \\ \vdots & \ldots & \vdots & \ldots \\ (1+\beta)\left(\sum_{i=1}^{I} M_{i1}^2\right)\delta_{dd} & \ldots & (1+\beta)\left(\sum_{i=1}^{I} M_{i1}^2\right)\delta_{dd} & \\ (1+\beta)\left(\sum_{i=1}^{I} M_{i1} M_{i2}\right)\delta_{d1} & & \ldots & \\ \vdots & & \vdots & \end{bmatrix} \tag{17}$$

$$h = \left[-2(P+\beta C)\left(\sum_{i=1}^{I} M_{i1}\right)\delta_1, \ldots, -2(P+\beta C)\left(\sum_{i=1}^{I} M_{i1}\right)\delta_d, \ldots, -2(P+\beta C)\left(\sum_{i=1}^{I} M_{iN}\right)\delta_d\right] \tag{18}$$

In S304, the optimization apparatus 200 employs J and h of the expressions (17) and (18) as the coupling coefficients (Q) and outputs them with Z=[$\alpha_W, \beta_W, \delta_w$]. Actually, numerical values are substituted into all places of symbols.

Referring back to FIG. 10, the optimization apparatus 200 executes processing based on simulated annealing (SA) by the Ising machine based on the coupling coefficients (Q) (203). In the simulated annealing, a search is made for numerical values of W' that represent the combination of the states of the respective bits with which the minimum value of the cost function F'(W) transformed to the Ising format is obtained (ground state).

Subsequently, the optimization apparatus 200 carries out reverse binary expansion for the numerical values of W' obtained by the simulated annealing of the Ising machine (204). Thereby, the optimization apparatus 200 finds W that correspond to the numerical values of W' and are continuous values. For example, the optimization apparatus 200 obtains Wn (continuous values) from the Ising spins (numerical values of W') based on the following expression (19) by using the coefficients $Z=[\alpha_W, \beta_W, \delta_w]$ of the binary expansion.

$$Wn \approx (\alpha_W - \beta_W)(\delta_W[1]*wd[1]+\delta_w[2]*wd[2]+ \ldots +\iota_w[dd]*wd[dd])+\beta_W \quad (19)$$

Here, the values of W', which are the result obtained from F'(W), are correct. However, because the term that is a discontinuous max function (F1(W)) is squared to be replaced by the q-loss function, W' are approximate values from the viewpoint of F(W) and are not correct values.

Figure 14:
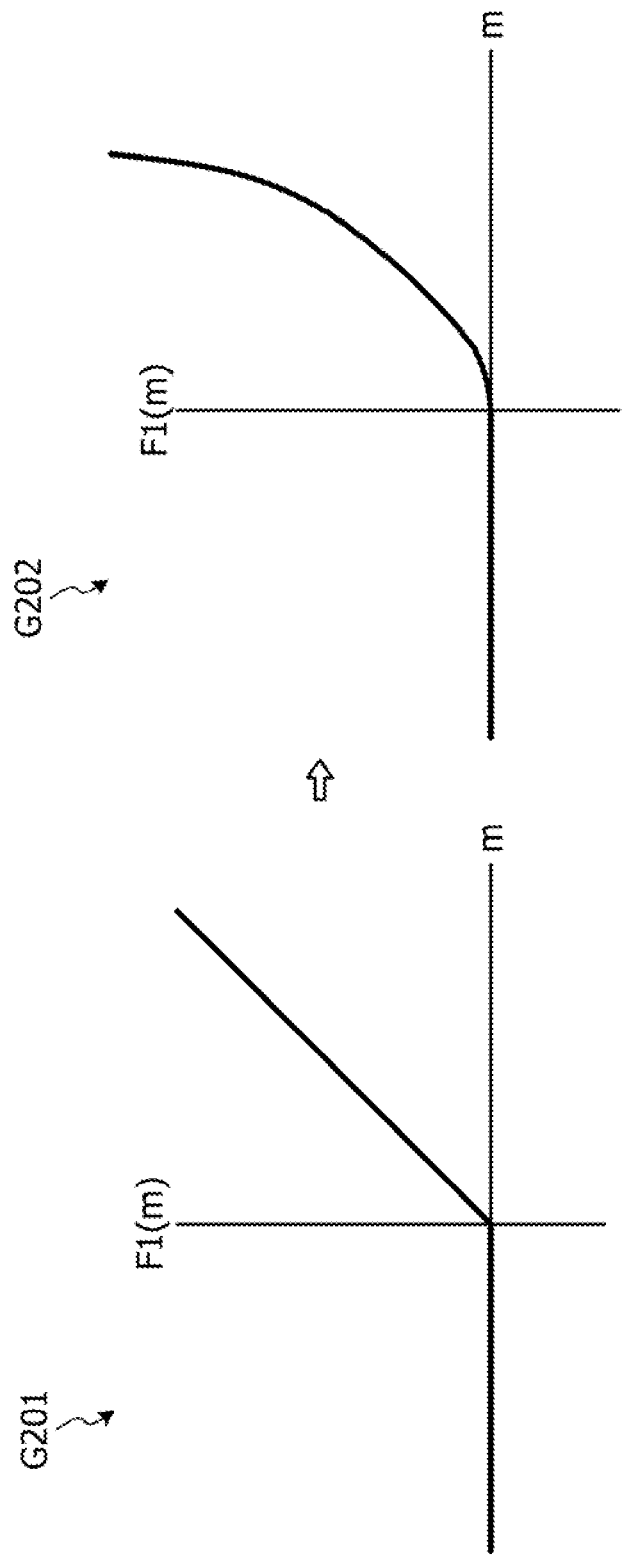
FIG. 14 is an explanatory diagram explaining an example of transformation by q-loss function.

FIG. 14 is an explanatory diagram explaining an example of transformation by q-loss function. For example, as illustrated in FIG. 14, a graph G201 is one example of F1(m)=max(0, m) as a term that is a discontinuous max function. In the replacement by use of the q-loss function, the term F1(W), which is the discontinuous max function, is squared. Due to this, the shape of the function (shape of the graph) changes as in a graph G202 that is one example of F1(m)=max(0, m)$^2$.

For example, in formulation of a radiation irradiation plan, it is important to impose correct constraint corresponding to the linearity represented in the graph G201 on the beams with which irradiation is carried out. However, if the linearity is not retained after the transformation as in the graph G202, it becomes difficult to impose the correct constraint and the constraint on the beams becomes less or becomes excessive in some cases.

FIG. 15 is an explanatory diagram exemplifying discontinuous functions. As illustrated in FIG. 15, as discontinuous functions that change in the shape of the function when being replaced by an Ising model, there are also −min(0, m) of a graph G203, max(m, −m) of a graph G204, and so forth. For example, in the case of −min(0, m) of the graph G203, the function becomes max(0, m) when m is subjected to variable transformation to −m. Thus, −min(0, m) may be treated similarly to max(0, m).

In one aspect, the embodiments discussed herein intend to provide an optimization apparatus, an optimization method, and an optimization program that enable finding of the optimum solution with higher accuracy.

The optimization apparatus, the optimization method, and the optimization program according to the embodiments will be described below with reference to the drawings. Configurations having the same function in the embodiments are given the same numeral and overlapping description is omitted. The optimization apparatus, the optimization method, and the optimization program described in the following embodiments merely represent one example and do not limit the embodiments. Furthermore, the following respective embodiments may be combined as appropriate in a range in which contradiction is not caused.

Figure 1:
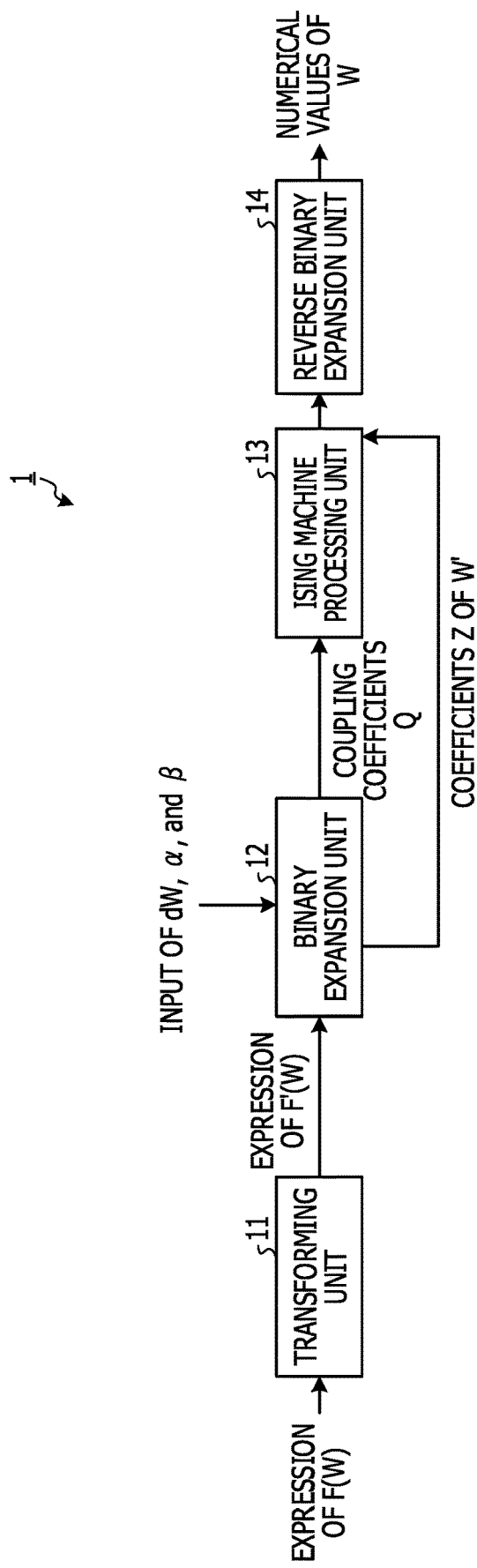
FIG. 1 is a block diagram illustrating a functional configuration example of an optimization apparatus according to an embodiment.

FIG. 1 is a block diagram illustrating a functional configuration example of an optimization apparatus according to an embodiment. As illustrated in FIG. 1, an optimization apparatus 1 includes a transforming unit 11, a binary expansion unit 12, an Ising machine processing unit 13, and a reverse binary expansion unit 14.

The transforming unit 11 is a processing unit that accepts input of a cost function F(W) relating to an optimization problem and carries out transformation to an expression of an Ising model (F'(W)) by using the Legendre transformation, the Lagrange function, and the Wolfe's duality theorem. Suppose that, in the present embodiment, the cost function F(W) input to the transforming unit 11 relates to the radiation irradiation plan exemplified in FIG. 11 as one example. For example, the input cost function F(W) is represented by the above-described expression (3).

The binary expansion unit 12 is a processing unit that subjects W to binary expansion into 0 and 1 for processing by an Ising machine because the transformed F'(W) remains continuous values. For example, similarly to the existing binary expansion (202), the binary expansion unit 12 turns values relating to coefficients of the cost function (F'(W)) transformed by the transforming unit 11 to the Ising format with binary spins through carrying out binary expansion.

The Ising machine processing unit 13 is a processing unit that executes processing based on simulated annealing (SA) by the Ising machine based on coupling coefficients (Q) and seeks values that represent the ground state.

The reverse binary expansion unit 14 carries out reverse binary expansion for the values that have been sought by the Ising machine processing unit 13 and represent the ground state, i.e. numerical values of W' obtained by the simulated annealing of the Ising machine. For example, the reverse binary expansion unit 14 executes the processing similar to that of the existing reverse binary expansion (204) and obtains continuous values (W) corresponding to the numerical values of W'. Thereby, the reverse binary expansion unit 14 obtains the values that minimize the input cost function F(W).

Figure 2:
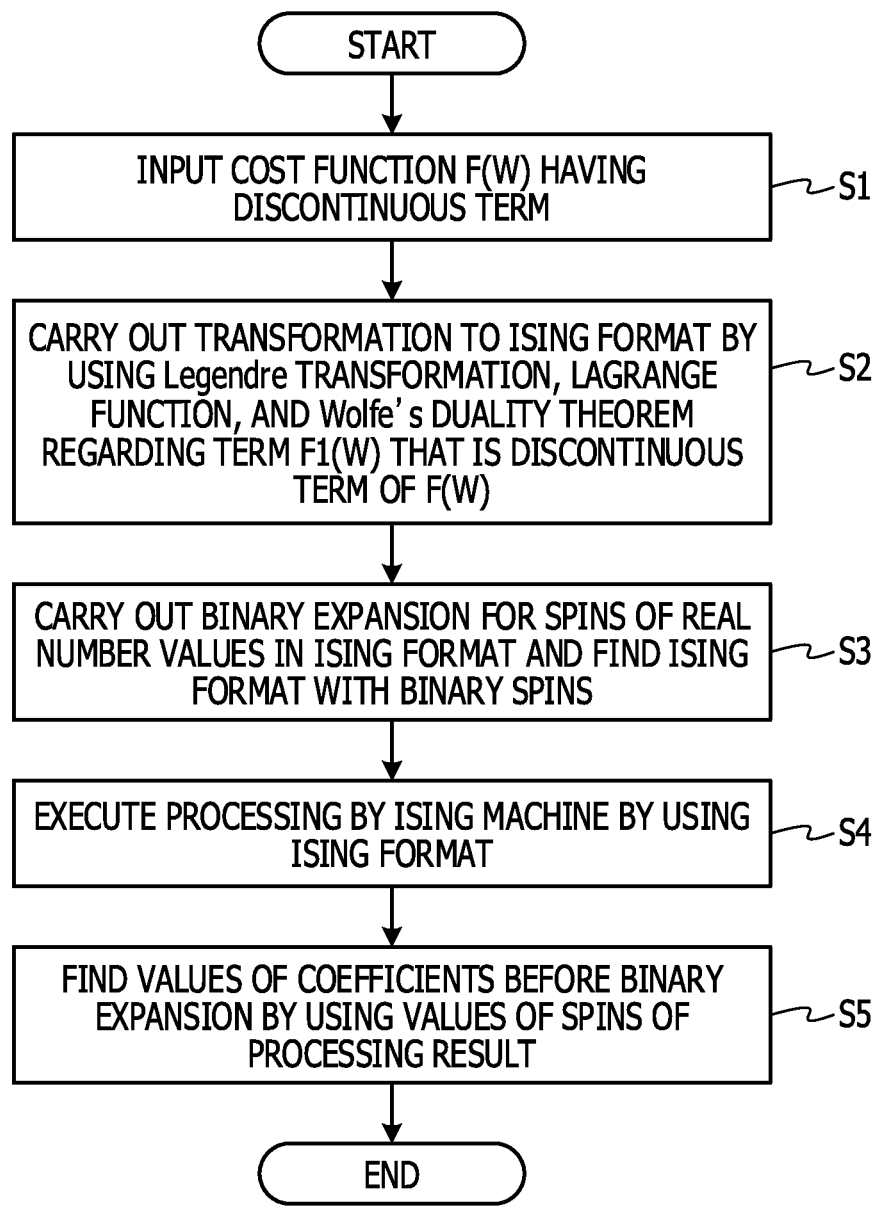
FIG. 2 is a flowchart illustrating an operation example of an optimization apparatus according to an embodiment.

Here, the processing of the respective units of the optimization apparatus 1 will be described in detail. FIG. 2 is a flowchart illustrating an operation example of an optimization apparatus according to the embodiment. The optimization apparatus illustrated by reference to FIG. 2 may be the optimization apparatus 1 illustrated in FIG. 1.

As illustrated in FIG. 2, when the processing is started, the transforming unit 11 accepts input of the cost function F(W) having a discontinuous term (F1(W)) (see expression (3)) (S1).

Here, the discontinuous term (F1(W)) is a second term ($\Sigma_i \beta_i$ max(0, di(w)−Ci)) in the cost function F(W) represented in expression (3). This discontinuous term may be specified by a user at the time of input of the cost function F(W) or may be detected from the cost function F(W) by a publicly-known expression processing system.

Subsequently, the transforming unit 11 carries out transformation to the Ising format by using the Legendre transformation, the Lagrange function, and the Wolfe's duality theorem regarding the term (F1(W)) that is the discontinuous term of the cost function F(W) (S2).

Figure 3:
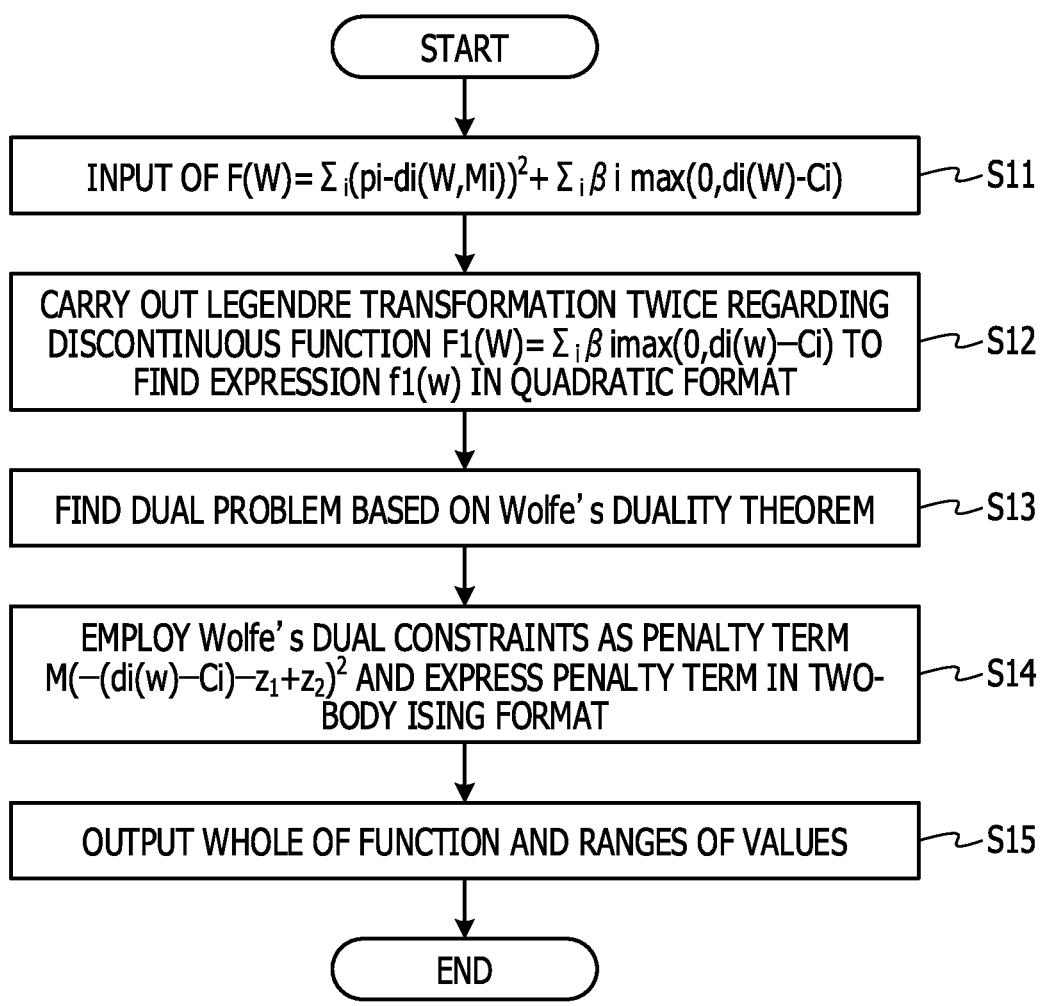
FIG. 3 is a flowchart exemplifying transformation processing.

Here, the transformation processing of S2 will be described in detail. FIG. 3 is a flowchart exemplifying transformation processing.

As illustrated in FIG. 3, when the processing is started, the transforming unit 11 accepts input of the cost function F(W) (see expression (3)) (S11). Subsequently, the transforming unit 11 carries out the Legendre transformation twice regarding the discontinuous function F1(W)=$\Sigma_i \beta_i$ max(0, di(w)−Ci), which is the discontinuous term in the cost function F(W). Thereby, the transforming unit 11 changes the variable of the function F1 that is convex downward and finds an expression f1(w) in the quadratic format (S12).

When the Legendre transformation is carried out regarding the discontinuous function, the nature does not change although the transformation is carried out because the resulting function is equivalently expressed by a set of tangents specified by the values of the slope and the intercept. For example, f*(p) resulting from the Legendre transformation of a function f is represented by the following expression (20).

$$f*(p) = \max_x\{px - f(x)\} = -\min_x\{f(x) - px\} \tag{20}$$

The transforming unit 11 carries out the Legendre transformation twice for $\beta_i \max(0, di(w)-Ci)$ of the discontinuous function F1(W). This is equivalent to operation of returning the function to the original because forward transformation and inverse transformation of the Legendre transformation are the same.

For example, f1(w)=max(0, di(w)−Ci)=−min(0, Ci−di(w)) is defined. When the Legendre transformation is carried out twice for the f1, setting m=di(w)−Ci and putting f1(m)=−min(0, m) yield the following expression (21).

$$f1(m) = \min_t\{-mt\} \text{ where } -1 \le t \le 0 \tag{21}$$

Figure 4:
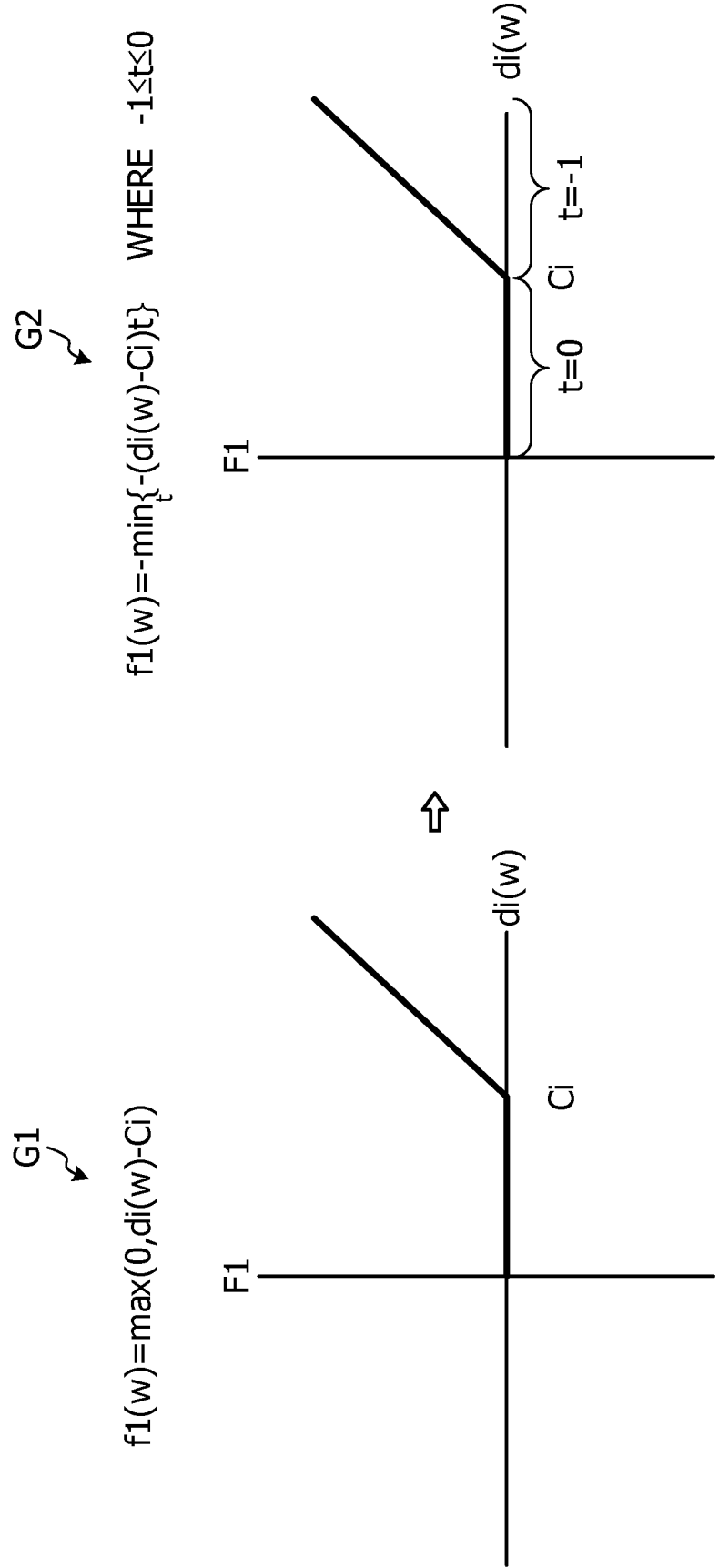
FIG. 4 is an explanatory diagram explaining one example of Legendre transformation.

FIG. 4 is an explanatory diagram explaining one example of Legendre transformation. In FIG. 4, a graph G1 is a graph of the discontinuous function F1 before the Legendre transformation. A graph G2 is a graph after the Legendre transformation is carried out twice for the discontinuous function F1. t is a variable added as the result of carrying out the Legendre transformation twice. The condition of t that minimizes (min)−(di(w)−Ci) of f1(w) of the graph G2 is t=0 for di(w)<Ci and t=−1 for di(w)>Ci. As illustrated in FIG. 4, regarding the discontinuous function, the nature of the graph does not change even when the Legendre transformation is carried out twice.

When the function (f1) after the Legendre transformation remains as it is, − (minus) sign exists in front of min of the function f1 and it is difficult to treat the function f1 as a minimization problem of m and t.

Therefore, the transforming unit 11 finds a dual problem based on the Wolfe's duality theorem regarding the function (f1) after the Legendre transformation (S13). For example, property that the original problem may also be solved if the dual problem may be solved is used.

For example, the following expression (22) is obtained when the dual problem is found regarding the function (f1). Here, $z_1$ and $z_2$ are Lagrange multipliers. m is m=di(w)−Ci.

$$\max_{t,z}\{-mt-z_1(t+1)+z_2t\}-m-z_1-z_2= 0, z_1 \ge 0, z_2 \ge 0, -1 \le t \le 0, \tag{22}$$

Furthermore, when the signs are reversed regarding expression (22), expression (23) is obtained.

$$-\min_{t,z}\{mt+z_1(t+1)-z_2t\} \tag{23}$$

Figure 5:
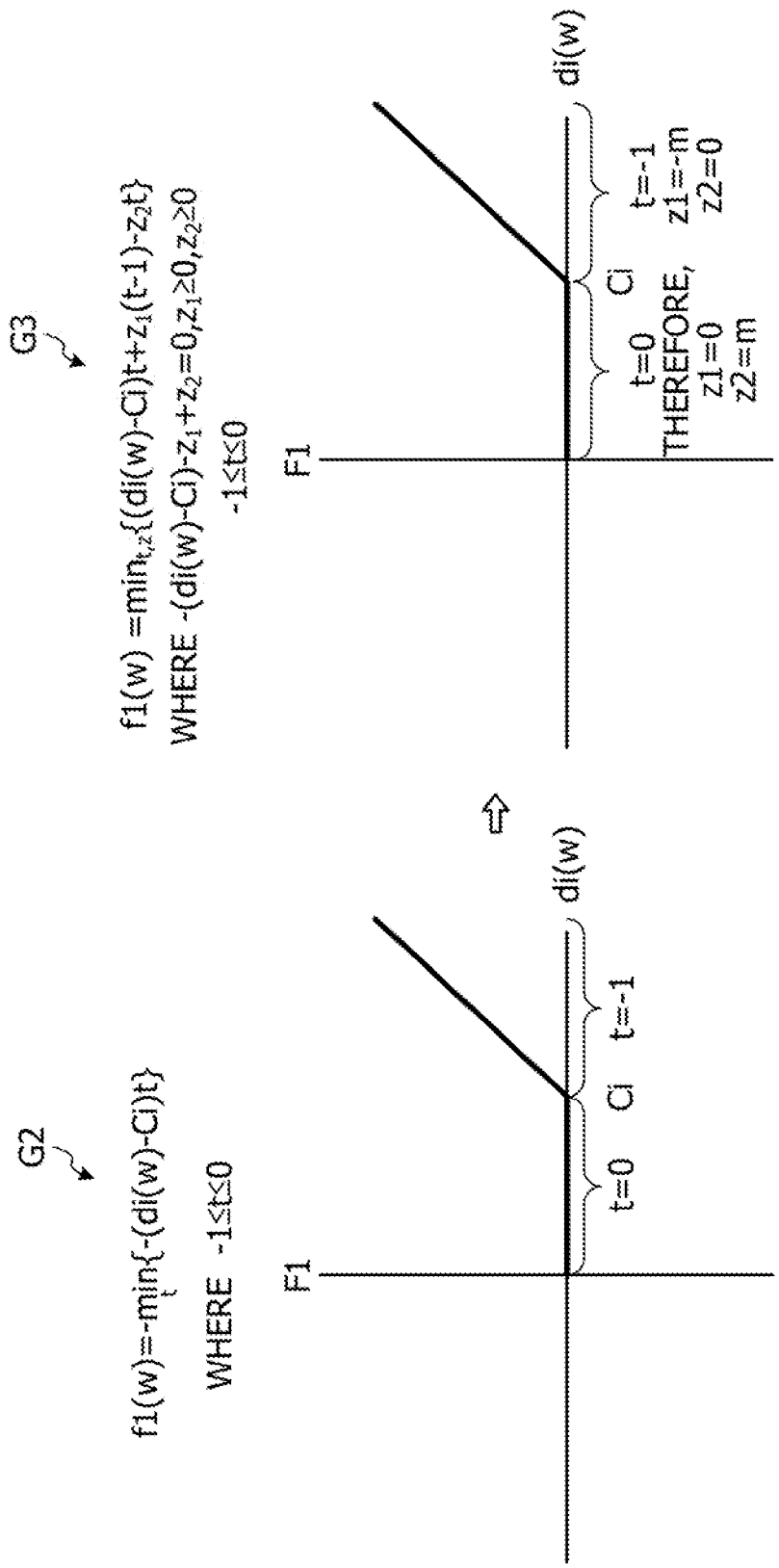
FIG. 5 is an explanatory diagram explaining one example of transformation by use of Wolfe's duality theorem.

FIG. 5 is an explanatory diagram explaining one example of transformation by use of Wolfe's duality theorem. In FIG. 5, the graph G2 is the graph after the Legendre transformation is carried out twice for the discontinuous function F1 as with FIG. 4. A graph G3 is a graph of the expression transformed through finding the dual problem based on the Wolfe's duality theorem.

As illustrated in FIG. 5, in the expression of the graph G3, $z_1$ and $z_2$ are added to t added when the Legendre transformation is carried out twice. In the graph G3, the condition of $z_1$ and $z_2$ that minimizes (min) f1(w) is $z_1$=0 for di(w)<Ci in order to cause f1(w) to follow the shape of the graph. Furthermore, for di(w)>Ci, $z_1$ and $z_2$ are indefinite, for example, they have no relation to the shape of the graph.

Referring back to FIG. 3, subsequently to S13, the transforming unit 11 employs Wolfe's dual constraints (expression transformed through finding the dual problem) as a penalty term $M(-(di(w)-Ci)-z_1+z_2)^2$ and expresses the penalty term in the two-body Ising format (S14). For example, the resulting function is represented by the following expression (24). M is set to a sufficiently large numerical value (for example, 100 or the like).

$$f1(w,t,z_1,z_2)=(di(w)-Ci)t+z_1(t+1)-z_2t+ M(-(di(w)-Ci)-z_1+z_2)^2 \tag{24}$$

Subsequently, regarding the cost function (F(W)), the transforming unit 11 outputs the whole of the function (F'(W)) in which the penalty term expressed in the two-body Ising format is incorporated instead of the discontinuous function (F1(W)) and the ranges of values.

For example, the output F'(W) is represented by the following expression (25). Furthermore, the output ranges of the values of $z_1$, $z_2$, and t are $z_1 \ge 0$, $z_2 \ge 0$, and $-1 \le t \le 0$.

$$\sum_i (pi - di(W, Mi))^2 + \tag{25}$$
$$\sum_i \beta i\{(di(w) - Ci)t + z_1(t+1) - z_2t + M(-(di(w) - Ci) - z_1 + z_2)^2\}$$

Referring back to FIG. 2, the Ising spins transformed to the Ising format in S2 are real number values. Therefore, subsequently to S2, the binary expansion unit 12 carries out binary expansion for the spins of the real number values in the Ising format and finds the Ising format with binary spins (S3). For example, the binary expansion unit 12 accepts input of the precision of the binary expansion (dw) and the range of values ($\alpha$, $\beta$) and carries out the binary expansion of W similarly to the existing binary expansion (202). Subsequently, the binary expansion unit 12 outputs coupling coefficients (Q) relating to W' resulting from the binary expansion and coefficients (Z) for returning W' to the original real numbers.

Subsequently, the Ising machine processing unit 13 executes processing by an Ising machine by using the Ising format (S4). For example, the Ising machine processing unit 13 executes processing based on simulated annealing (SA) by the Ising machine based on the coupling coefficients (Q) and finds the values of the respective spins that represent the ground state.

Subsequently, the reverse binary expansion unit 14 finds the values of coefficients before the binary expansion by using the values of the spins of the processing result by the Ising machine (values of the respective spins that represent the ground state) (S5). For example, the reverse binary expansion unit 14 executes the processing similar to that of the existing reverse binary expansion (204) to carry out reverse binary expansion for the numerical values of W' obtained by the Ising machine. Thereby, the optimization apparatus 1 obtains the values (real number values) that minimize the input cost function F(W).

As described above, the optimization apparatus 1 includes the transforming unit 11, the binary expansion unit 12, the Ising machine processing unit 13, and the reverse binary expansion unit 14. The transforming unit 11 transforms an input first cost function (F(W)) to a second cost function (F'(W)) by using the Lagrange function and the Wolfe's duality theorem. The binary expansion unit 12 finds the coupling coefficients (Q) to turn values relating to the coefficients of the second cost function to the Ising format with binary spins through carrying out binary expansion. The Ising machine processing unit 13 seeks the values that represent the ground state regarding the coupling coefficients relating to the second cost function (F'(W)). The reverse binary expansion unit 14 carries out reverse binary expansion regarding the sought values that represent the ground state and finds the values that minimize the first cost function (F(W)).

Due to this, when describing the absolute value constraint included in the first cost function (F(W)) by an Ising model, the optimization apparatus 1 may treat the absolute value constraint as it is without changing the shape of the function (graph shape). Therefore, the optimization apparatus 1 may find the optimum solution with higher accuracy.

Figure 6:
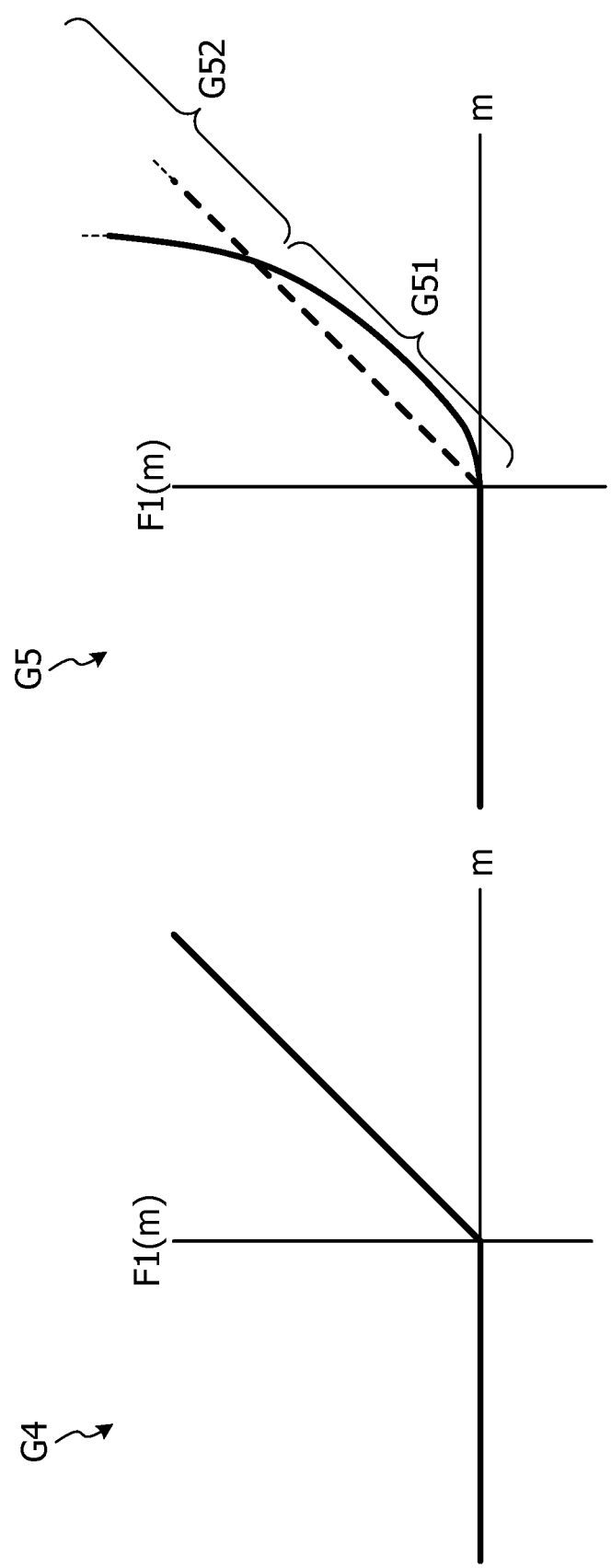
FIG. 6 is an explanatory diagram illustrating a comparative example between the present embodiment and an existing method regarding a discontinuous function.

FIG. 6 is an explanatory diagram illustrating a comparative example between the present embodiment and an existing method regarding a discontinuous function. In FIG. 6, a graph G4 is a graph when a discontinuous function F1(m) is described by an Ising model by the transforming unit 11. A graph G5 is a graph when the discontinuous function F1(m) is described by an Ising model by the existing method using the q-loss function.

As illustrated in FIG. 6, in the graph G4, the function may be treated with the graph shape corresponding to the max function remaining as is (with the absolute value constraint remaining as it is). In contrast, in the existing method, the linearity is not retained in the graph shape after the transformation, and a region G51 in which the constraint becomes less and a region G52 in which the constraint becomes excessive are generated. As a result, for example, in formulation of a radiation irradiation plan, the constraint on beams becomes less or becomes excessive in some cases.

FIG. 7 is an explanatory diagram explaining one example of an experimental result. The experimental result illustrated in FIG. 7 is obtained by finding a radiation irradiation plan when tumors (disease P(2) to P(4)) and normal tissue (normal P(1)) are disposed as a pixel arrangement P1. Beams exist at 20 places in a clockwise manner and the irradiation amount (M) is as represented in FIG. 7, with the number of rows being I and the number of columns being N. Furthermore, suppose that the values of P(1 to 5) and the values of Ci are as represented in FIG. 7. Moreover, suppose that square constraint using the q-loss function may be used if the result of multiplication of the obtained intensity W and M does not surpasses Ci (here Ci=P+0.01).

In FIG. 7, MWabs is the result of multiplication of the obtained W and M (with absolute value constraint) by the optimization apparatus 1 of the present embodiment under the conditions represented in FIG. 7. Furthermore, MWsquare is the result of multiplication of the obtained W and M (with square constraint) by the existing optimization apparatus 200. As illustrated in FIG. 7, in MWsquare, the first and third values are larger than Ci and excessive. In contrast, in MWabs, a value that exceeds Ci does not exist. Therefore, it turns out that the constraint on the beams effectively works in the radiation irradiation plan by the optimization apparatus 1 of the present embodiment.

Furthermore, the transforming unit 11 carries out the Legendre transformation regarding the discontinuous function (F1(W)) included in the first cost function (F(W)). Then, the transforming unit 11 carries out transformation to the second cost function (F'(W)) by incorporating a function obtained through finding a dual problem based on the Wolfe's duality theorem based on the expression after the Legendre transformation to the first cost function instead of the discontinuous function. This allows the optimization apparatus 1 to carry out the transformation from the first cost function (F(W)) to the second cost function (F'(W)) without changing the shape of the discontinuous function (graph shape) included in the first cost function (F(W)).

The respective constituent elements of the respective apparatuses that are diagrammatically represented do not necessarily be configured as diagrammatically represented physically. For example, specific forms of distribution and integration of the respective apparatuses are not limited to the diagrammatically-represented forms, and all or part of the respective apparatuses may be configured to be distributed or integrated functionally or physically in an arbitrary unit according to various loads, the status of use, and so forth.

All or an arbitrary part of various processing functions executed in the optimization apparatus 1 may be executed on a central processing unit (CPU) (or microcomputer such as micro-processing unit (MPU) or micro controller unit (MCU)). Furthermore, it goes without saying that all or an arbitrary part of various processing functions may be executed on a program analyzed and executed by the CPU (or microcomputer such as MPU or MCU) or hardware based on wired logic. Moreover, the various processing functions executed in the optimization apparatus 1 may be executed through cooperation of plural computers based on cloud computing.

Figure 8:
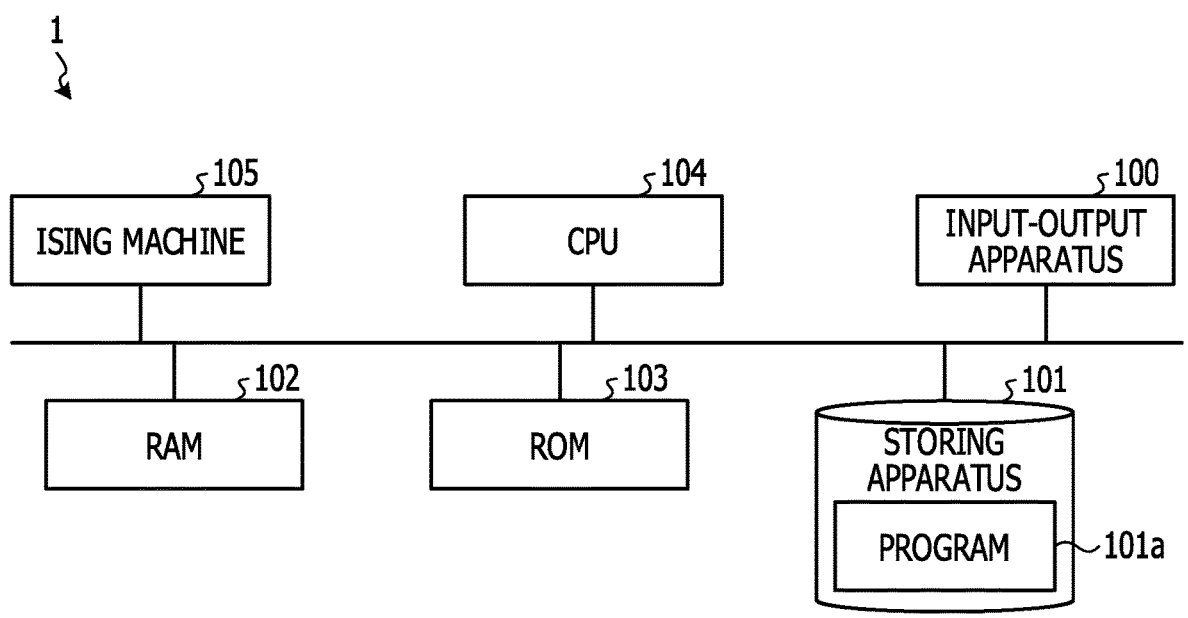
FIG. 8 is a block diagram illustrating a hardware configuration example of an optimization apparatus according to an embodiment.

Incidentally, various kinds of processing explained in the above-described embodiment may be implemented by executing a program prepared in advance by a computer. Thus, one example of a computer (hardware) that executes a program having the functions similar to that of the above-described embodiment will be described below. FIG. 8 is a block diagram illustrating a hardware configuration example of an optimization apparatus according to the embodiment. The optimization apparatus illustrated in FIG. 8 may be the optimization apparatus 1 illustrated in FIG. 1.

As illustrated in FIG. 8, the optimization apparatus 1 includes an input-output apparatus 100, a storing apparatus 101, a random access memory (RAM) 102, a read only memory (ROM) 103, a CPU 104, and an Ising machine 105. The respective units (100 to 105) in the optimization apparatus 1 are coupled to a bus 106.

The input-output apparatus 100 is an input apparatus such as keyboard and mouse that accept input operation from a user and an output apparatus such as a display that outputs various processing results. The storing apparatus 101 is a hard disk apparatus or the like, for example, and a program 101a for executing various kinds of processing explained in the above-described embodiment is stored therein. Furthermore, various kinds of data to which the program 101a refers are stored in the storing apparatus 101. The RAM 102 is used when the CPU 104 reads out the program 101a and executes various kinds of processing, and temporarily stores various kinds of information. The ROM 103 is a non-volatile memory that stores a boot program executed at the time of activation of the optimization apparatus 1, and so forth, for example.

The CPU 104 executes various kinds of processing relating to the transforming unit 11, the binary expansion unit 12, the Ising machine processing unit 13, and the reverse binary expansion unit 14 by reading out the program 101a stored in the storing apparatus 101 and loading the program 101a into the RAM 102 to execute it. The program 101*a* does not have to be stored in the storing apparatus 101. For example, the optimization apparatus 1 may read out and execute the program 101*a* stored in a storage medium that may be read by the optimization apparatus 1. The storage medium that may be read by the optimization apparatus 1 is compact disc (CD)-ROM, digital versatile disc (DVD) disc, portable recording medium such as universal serial bus (USB) memory, semiconductor memory such as flash memory, hard disk drive, and so forth, for example. Furthermore, the program 101*a* may be stored in an apparatus coupled to a public line, the Internet, a local area network (LAN), or the like and the optimization apparatus 1 may read out the program 101*a* from any of them and execute it.

The Ising machine 105 is an apparatus that executes processing based on simulated annealing (SA) and seeks the combination of the states of the respective bits with which the minimum value of a cost function transformed to the Ising format is obtained (ground state) under control by the Ising machine processing unit 13.

Figure 9:
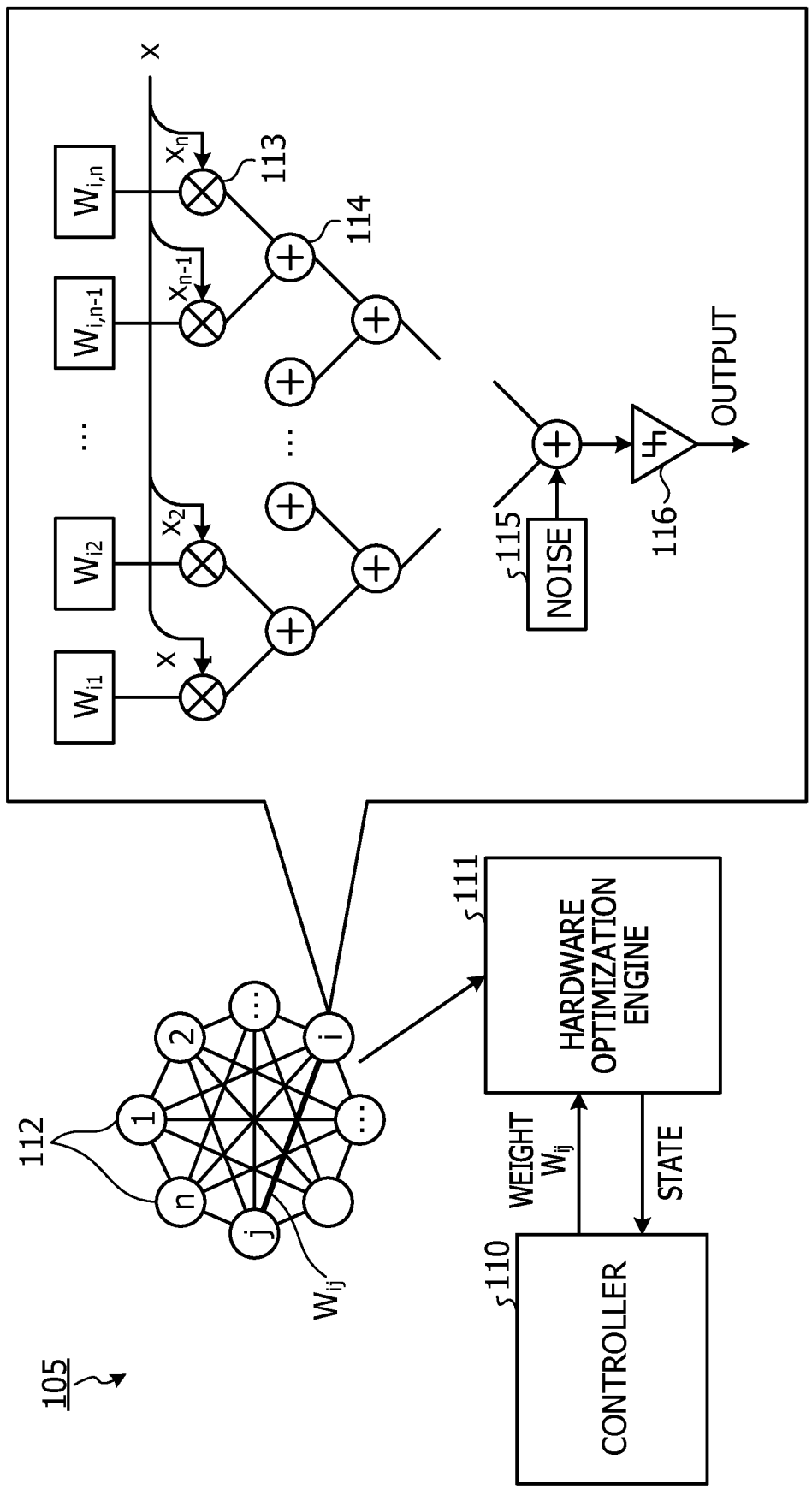
FIG. 9 is an explanatory diagram explaining one example of an Ising machine.

FIG. 9 is an explanatory diagram explaining one example of an Ising machine. The Ising machine illustrated in FIG. 9 may be the Ising machine 105 illustrated in FIG. 8. As illustrated in FIG. 9, the Ising machine 105 includes a controller 110, a hardware optimization engine 111, and plural neurons 112.

The controller 110 passes weights $W_{ij}$ relating to coupling coefficients to the hardware optimization engine 111 and causes the hardware optimization engine 111 to execute simulated annealing (SA) processing to obtain the state of each bit. The hardware optimization engine 111 sets the weights $W_{ij}$ from the controller 110 in each of the neurons 112 and obtains output after the SA processing from each of the neurons 112. Subsequently, the hardware optimization engine 111 outputs, to the controller 110, the output obtained from each of the neurons 112.

The plural neurons 112 are what are obtained by modeling an Ising model by using a neural network. For example, each of the plural neurons 112 functions as a neuron that outputs 0 or 1 according to the states of the other bits and the weights $W_{ij}$ (coupling coefficients) that represent the strength of coupling between another bit and the self-bit.

For example, each of the neurons 112 includes multipliers 113, adders 114, and a comparator 116. Each of the multipliers 113 multiplies the states $(x_1, x_2, \ldots, x_n)$ of n neurons 112 output from the hardware optimization engine 111 and the weights $W_{i1}, \ldots,$ and $W_{i,n}$. The adders 114 integrate the values output from the multipliers 113 and adds noise 115. The comparator 116 outputs a comparison result between the value resulting from the integration by the adders 114 and the addition of the noise 115 and a threshold. The neuron 112 seeks the ground state by sequentially updating the parameters of the neuron 112 based on the output value obtained from the comparator 116 and repeating the processing.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. An optimization apparatus comprising:

a memory; and a processor coupled to the memory, the processor coupled to an Ising machine, the processor being configured to receive an input information indicating a first cost function regarding a radiation irradiation plan in a medical field, the first cost function being a numerical expression including a part being a continuous function and a part being a discontinuous function, the discontinuous function including an organ-dependent irradiation limit in the radiation irradiation plan;

transform the first cost function indicated by the received input information to a second cost function by using at least "Legendre transformation" and "Wolfe's duality theorem," in order to obtain the second cost function without changing a graph shape of the discontinuous function included in the first cost function;

acquire first values being values in an Ising format by performing binary expansion on values relating to coefficients of the second cost function obtained by the transforming from the first cost function;

output the first values to the Ising machine and cause the Ising machine to perform a simulated annealing (SA) on the second cost function to seek values that represent a ground state regarding the first values in the Ising format relating to the coefficients of the second cost function;

receive, from the Ising machine, a result including the sought values that represent the ground state;

in response to the receiving of the result from the Ising machine, execute reverse binary expansion processing that includes acquiring second values being values that minimize the first cost function by carrying out reverse binary expansion for the sought values that represent the ground state, and in response to the acquiring of the second values, output the radiation irradiation plan optimized based on the acquired second values, the outputted radiation irradiation plan being a radiation irradiation plan to be used in a radiation therapy to irradiate a tumor of a patient while reducing irradiation of normal tissue of the patient, wherein the transforming of the first cost function is configured to:

perform the Legendre transformation twice on the part being the discontinuous function included in the first cost function; and perform transformation to the second cost function from the first cost function by replacing the discontinuous function included in the first cost function to a first function, the first function being a function obtained through finding a Wolfe dual problem with respect to the first cost function expression that has undergone the Legendre transformation twice, the Wolfe dual problem being a dual problem of "Wolfe's duality theorem".

2. A method implemented by an optimization apparatus, the optimization apparatus comprises a processor coupled to an Ising machine, the method comprising:

Receiving, by the processor, an input information indicating a first cost function regarding a radiation irradiation plan in a medical field, the first cost function being a numerical expression including a part being a continuous function and a part being a discontinuous function, the discontinuous function including an organ-dependent irradiation limit in the radiation irradiation plan;

Transforming, by the processor, the input first cost function indicated by the received input information to a second cost function by using at least "Legendre transformation" and "Wolfe's duality theorem," in order to obtain the second cost function without changing a graph shape of the discontinuous function included in the first cost function;

Acquiring, by the processor, first values being values in an Ising format by performing binary expansion on values relating to coefficients of the second cost function obtained by the transforming from the first cost function;

Outputting, by the processor, the first values to the Ising machine, and causing the Ising machine to perform a simulated annealing (SA) on the second cost function to seek values that represent a ground state regarding the first values in the Ising format relating to the coefficients of the second cost function;

receiving, from the Ising machine, a result including the sought values that represent the ground state;

in response to the receiving of the result from the Ising machine, executing, by the processor, reverse binary expansion processing that includes acquiring values that minimize the first cost function by carrying out reverse binary expansion for the sought values that represent the ground state; and in response to the acquiring of the second values, output, by the processor, the radiation irradiation plan optimized based on the acquired second values, the outputted radiation irradiation plan being a radiation irradiation plan to be used in a radiation therapy to irradiate a tumor of a patient while reducing irradiation of normal tissue of the patient, wherein the transforming of the first cost function is configured to:

perform the Legendre transformation twice on the part being the discontinuous function included in the first cost function; and perform transformation to the second cost function from the first cost function by replacing the discontinuous function included in the first cost function to a first function, the first function being a function obtained through finding a Wolfe dual problem with respect to the first cost function expression that has undergone the Legendre transformation twice, the Wolfe dual problem being a dual problem of "Wolfe's duality theorem".

3. A non-transitory computer-readable storage medium for storing a program which causes a processor to perform processing, the processor coupled to an Ising machine, the processing comprising:

Receiving, by the processor, an input information indicating a first cost function regarding a radiation irradiation plan in a medical field, the first cost function being a numerical expression including a part being a continuous function and a part being a discontinuous function, the discontinuous function including an organ-dependent irradiation limit in the radiation irradiation plan;

Transforming, by the processor, the first cost function indicated by the received input information to a second cost function by using at least "Legendre transformation" and "Wolfe's duality theorem," in order to obtain the second cost function without changing a graph shape of the discontinuous function included in the first cost function;

Acquiring, by the processor, first values being values in an Ising format by performing binary expansion on values relating to coefficients of the second cost function obtained by the transforming from the first cost function;

Outputting, by the processor, the first values to the Ising machine, and causing the Ising machine to perform a simulated annealing (SA) on the second cost function to seek values that represent a ground state regarding the first values in the Ising format relating to the coefficients of the second cost function;

receiving, from the Ising machine, a result including the sought values that represent the ground state;

in response to the receiving of the result from the Ising machine, executing reverse binary expansion processing that includes acquiring second values being values that minimize the first cost function by carrying out reverse binary expansion for the sought values that represent the ground state; and in response to the acquiring of the second values, output the radiation irradiation plan optimized based on the acquired second values, the outputted radiation irradiation plan being a radiation irradiation plan to be used in a radiation therapy to irradiate a tumor of a patient while reducing irradiation of normal tissue of the patient, wherein the transforming of the first cost function is configured to:

perform the Legendre transformation twice on the part being the discontinuous function included in the first cost function; and perform transformation to the second cost function from the first cost function by replacing the discontinuous function included in the first cost function to a first function, the first function being a function obtained through finding a Wolfe dual problem with respect to the first cost function expression that has undergone the Legendre transformation twice, the Wolfe dual problem being a dual problem of "Wolfe's duality theorem".

\* \* \* \* \*